US008846878B1

(12) United States Patent  
Karalus et al.

(10) Patent No.: US 8,846,878 B1  
(45) Date of Patent: Sep. 30, 2014

(54) METHOD AND DEVICE FOR ISOLATING A PROTEIN SAMPLE

(75) Inventors: Richard J. Karalus, Alden, NY (US); David R. Pawlowski, Getzville, NY (US)

(73) Assignee: CUBRC Corporation, Buffalo, NY (US)

( * ) Notice: Subject to any disclaimer, the term of this patent is extended or adjusted under 35 U.S.C. 154(b) by 629 days.

(21) Appl. No.: 12/692,194

(22) Filed: Jan. 22, 2010

Related U.S. Application Data

(60) Provisional application No. 61/205,794, filed on Jan. 23, 2009.

(51) Int. Cl.
| | |
|---|---|
| C07H 1/08 | (2006.01) |
| C07H 21/04 | (2006.01) |
| C07K 14/00 | (2006.01) |

(52) U.S. Cl.  
USPC .......................................... 530/417; 536/23.1

(58) Field of Classification Search  
None  
See application file for complete search history.

(56) References Cited

U.S. PATENT DOCUMENTS

| | | | |
|---|---|---|---|
| 3,698,561 | A | 10/1972 | Babson |
| 3,985,032 | A | 10/1976 | Avakian |
| 4,563,104 | A | 1/1986 | Saint-Amand |
| 4,933,291 | A | 6/1990 | Daiss et al. |
| 5,171,537 | A | 12/1992 | Wainwright et al. |
| 5,346,994 | A | 9/1994 | Chomczynski |
| 5,876,918 | A | 3/1999 | Wainwright et al. |
| 5,945,515 | A | 8/1999 | Chomczynski |
| 6,143,252 | A | 11/2000 | Haxo |
| 6,368,800 | B1 | 4/2002 | Smith et al. |
| 6,482,362 | B1 | 11/2002 | Smith |
| 6,610,488 | B2 | 8/2003 | Danenberg et al. |
| 7,595,026 | B2 | 9/2009 | Hudson et al. |
| 2002/0032317 | A1 * | 3/2002 | Blank .......................... 530/413 |
| 2004/0224344 | A1 | 11/2004 | Han et al. |
| 2007/0215543 | A1 | 9/2007 | Haidle |
| 2009/0081084 | A1 | 3/2009 | Douglas et al. |
| 2009/0107927 | A1 | 4/2009 | Belgrader |
| 2009/0111193 | A1 | 4/2009 | Cooney et al. |

FOREIGN PATENT DOCUMENTS

| | | |
|---|---|---|
| WO | 20081103828 | 8/2008 |
| WO | 20091058414 | 5/2009 |
| WO | 20091058432 | 5/2009 |

OTHER PUBLICATIONS

Tolosa et al., "Column-based method to simultaneously extract DNA, RNA, and proteins from the same sample", BioTechniques 43: 799-804 (Dec. 2007).*

Callesen et al., "Serum protein profiling by solid phase extraction and mass spectrometry: a future diagnostics tool?" Proteomics 9: 1428-1441 (2009).

Dauphin et al., "Evaluation of five commercial nucleic acid extraction kits for their ability to inactivate *Bacillus anthracis* spores and comparison of DNA yields from spores and spiked environmental samples." Journal of Microbiological Methods 76: 30-37 (2009).

Parida et al., "Adsorption of organic molecules on silica surface." Advances in Colloid and Interface Science 121: 77-110 (2006).

Read SJ "Recovery efficiencies of nucleic acid extraction kits as measured by quantitative LightCyclerTM PCR." Mol Pathol 54: 86-90 (2001).

Boom et al., "Rapid and simple method for purification of nucleic acids." J. Clin. Microbial. 28 (3), 495-503 (1990).

Feng et al., "Multiplex PCR for detection of trait and virulence factors in enterohemorrhagic *Escherichia coli* serotypes." Mol. Cell. Probes. 14 (6), 333-337 (2000).

Banerjee et al., "Quantitative recovery of immunoreactive proteins from clinical samples following RNA and DNA isolation." BioTechniques., vol. 35, No. 3, pp. 450-456 (2003).

Berglund et al., "Optimized Methodology for Sequential Extraction of RNA and Protein from Small Human Skin Biopsies."Optimized Methodology for Sequential Extraction of RNA and Protein from Small Human Skin Biopsies. Journal of Investigative Dermatology., pp. 349-53, vol. 127 (2007).

Butt et al., "Enabling Coupled Quantitative Genomics and Proteomics Analyses from Rat Spinal Cord Samples." Molecular & Cellular Proteomics., vol. 6.9., pp1574-88 (2007).

Hummon et al., "Isolation and solubilization of proteins after TRIzol® extraction of RNA and DNA from patient material following prolonged storage." BioTechniques., vol. 42, No. 4: pp. 467-472 (2007).

Morse et al., "Concurrent mRNA and protein extraction from the same experimental sample using a commercially available column-based RNA preparation kit." BioTechniques 40:54-58 (2006).

Riol et al., "Optimized Lymphocyte Protein Extraction Performed Simultaneously with DNA and RNA Isolation: Application to the Study of Factors Affecting DNA, RNA, and Protein Recovery from Lymphocytes of the Oldest Individuals." Analytical Biochemistry., vol. 275, Issue 2, pp. 192-201 (1999).

* cited by examiner

*Primary Examiner* — Anand Desai  
(74) *Attorney, Agent, or Firm* — Phillips Lytle LLP

(57) ABSTRACT

A novel method for recovering nucleic acids and proteins from a biological sample having the steps of mixing a biological sample with a nucleic acid binding solution and contacting the mixture with a first porous silica compound configured to reversibly bind a nucleic acid. The fluid remainder of the mixture is gathered for protein extraction. The first silica compound is contacted with a nucleic acid elution solution which causes a majority of the nucleic acid bound to the first porous silica compound to unbind and enter the solution phase. The solution is collected, which contains isolated nucleic acid. The fluid gathered for protein extraction is mixed with a protein binding solution and contacted with a protein binding porous silica compound configured to reversibly bind a protein. The fluid remainder is separated from the protein binding porous silica compound. A protein elution solution is contacted with the protein binding porous silica compound to cause a majority of the protein bound to the protein binding porous silica compound to unbind and enter the solution phase, allowing the protein to be isolated.

49 Claims, 6 Drawing Sheets

FIG. 2
Gel Analysis of Recovered Protein
Sup35NM Prion Surrogate
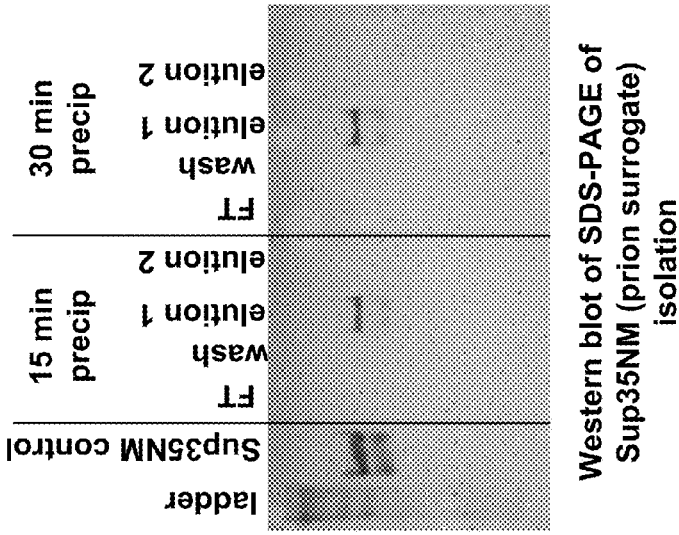
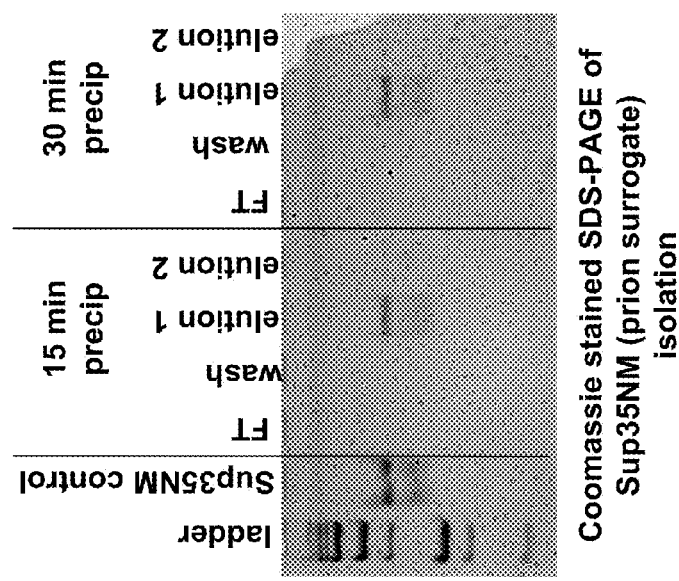

FIG. 5
Gel Analysis of Recovered Protein from *Y. pestis*

SDS-PAGE of *Y. pestis* profile

Western of *Y. pestis* profile
Rabbit anti-Y. pestis (CRP)

Gel Analysis of Recovered Protein

METHOD AND DEVICE FOR ISOLATING A PROTEIN SAMPLE

CROSS-REFERENCE TO RELATED APPLICATIONS

This application claims the benefit of U.S. Provisional Patent Application No. 61/205,794, filed Jan. 23, 2009. The entire content of such application is incorporated by reference herein.

TECHNICAL FIELD

The present invention relates to methods for isolating materials from a sample, and, more particularly, to a method and a kit for isolating proteins from a biological sample.

BACKGROUND ART

There are a number of known methods for isolating DNA, RNA and proteins from biological material. For example, it is known that an ultra-centrifugation of a sample homogenate in a guanidine-cesium chloride solution may be employed. The sample may be homogenized in 4 molar (M) guanidine thiocyanate and then over-layered on a cesium chloride (CsCl) solution and centrifuged at greater than 100,000 g for a long period of time. Following centrifugation, DNA, RNA and proteins may be separated and purified.

U.S. Pat. No. 5,346,994 teaches a method of isolating DNA, RNA and proteins based on liquid-phase separation using phenol and guanidine thiocyanate. A biological sample is homogenized in an aqueous solution of phenol and guanidine thiocyanate and the homogenate thereafter is mixed with chloroform. Following centrifugation, the homogenate separates into an organic phase, an interphase and an aqueous phase. Proteins are sequestrated into the organic phase, DNA into the interphase and RNA into the aqueous phase.

U.S. Pat. No. 5,945,515 discloses a product and process for isolating DNA, RNA and proteins with a solution that includes effective amounts of chaotropic agent, buffer, reducing agent, and water, with or without organic solvents.

Other conventional protocols generally entail use of phenol or an organic solvent mixture containing phenol and chloroform to extract proteins and lipids from a conventional lysate solution. The phenol/chloroform extraction step is generally followed by precipitation of the nucleic acid material remaining in the extracted aqueous phase by adding ethanol to that aqueous phase. The precipitate is typically removed from the solution by centrifugation, and the resulting pellet of precipitate is allowed to dry before being re-suspended in water or a buffer solution for further processing or analysis.

SUMMARY

With parenthetical reference to the corresponding parts portions or surfaces of the disclosed embodiment, merely for the purposes of illustration and not by way of limitation, the present invention provides a method for recovering nucleic acids and proteins from a biological sample comprising the steps of: (a) providing a biological sample; (b) providing a nucleic acid binding solution; (c) mixing the biological sample with the nucleic acid binding solution; (d) providing a first porous silica compound configured to reversibly bind a nucleic acid; (e) contacting a product of step (c) with the first porous silica compound; (f) separating a fluid product of step (e) from the first porous silica compound; (g) providing a nucleic acid elution solution; (h) contacting the nucleic acid elution solution with the first porous silica compound after step (f) to cause a majority of the nucleic acid bound to the porous silica compound to unbind; (i) collecting the unbound nucleic acid; (j) providing a protein binding solution; (k) mixing the fluid product of step (f) with the protein binding solution; (l) providing a protein binding porous silica compound configured to reversibly bind a protein; (m) contacting a product of step (k) with the protein binding porous silica compound; (n) separating a fluid product of step (m) from the protein binding porous silica compound; (o) providing a protein elution solution; (p) contacting the protein elution solution with the protein binding porous silica compound after step (m) to cause a majority of the protein bound to the protein binding porous silica compound to unbind; and (q) collecting the unbound protein.

The biological sample may comprise cells or viruses. The nucleic acid binding solution may include a chaotropic agent. The nucleic acid binding solution may consist solely of a chaotropic agent. The nucleic acid binding solution may comprise a lysate. The nucleic acid binding solution may lyse the biological sample. The chaotropic agent may be selected from a group consisting of urea, guanidine salts, and lithium perchlorate. The nucleic acid binding solution may comprise a detergent. The detergent may be selected from a group consisting of sodium dodecyl sulfate (SDS), polyoxyethylene sorbitan monooleate, and polyethylene glycol p-(1,1,3,3-tetramethylbutyl)-phenyl ether. The first porous silica compound may be in a form selected from a group consisting of a silica syringe filter, a silica matrix, a silica frit, a silica particulate column, and a silicate pipette tip. The nucleic acid elution solution may comprise water and a salt.

The protein binding solution may be selected from a group consisting of isopropanol, ethanol, trichloroacetic acid, acetone, and methanol. The protein binding solution may comprise a precipitating catalyst. The precipitating catalyst may comprise glycogen. The protein binding solution may comprise a detergent. The detergent of the protein binding solution may be selected from a group consisting of sodium dodecyl sulfate, polyoxyethylene sorbitan monooleate, and polyethylene glycol p-(1,1,3,3-tetramethylbutyl)-phenyl ether.

The protein elution solution may comprise water and a salt. The protein elution solution may comprise a detergent. The detergent in the protein elution solution may be selected from a group consisting of sodium dodecyl sulfate, polyoxyethylene sorbitan monooleate, and polyethylene glycol p-(1,1,3,3-tetramethylbutyl)-phenyl ether.

The method may further comprise the step of incubating a product of step (k) for a period of time. The period of incubation may be less than about 60 minutes. The period of incubation may be less than about five minutes.

The method may further comprise the step of contacting a wash solution with the first porous silica compound after step (e) and before step (h), and contacting the wash solution with the first porous silica compound may be performed directly after step (e). The nucleic acid wash solution may comprise ethanol or acetone. The method may further comprise the step of contacting a wash solution with the protein binding porous silica compound after step (m) and before step (p), and contacting the wash solution with the protein binding porous silica compound may be performed directly after step (m). The second wash solution may be isopropanol. The method may further comprise the step of drying the first porous silica compound after the step of contacting the first porous silica compound with the washing solution. The method may further comprise the step of drying the protein binding porous silica compound after the step of contacting the protein binding porous silica compound with the washing solution.

The protein binding porous silica compound may be in a form selected from a group consisting of a silica syringe filter, a silica matrix, a silica frit, a silica particulate column, and a silicate pipette tip. The protein binding porous silica compound may be borosilicate. The first porous silica compound and the protein binding porous silica compound may be the same. Each of the first and protein binding porous silica compounds may comprise a paramagnetic material.

Each of the contacting steps (e) and (m) may comprise the step of applying an external force to pass the products through the porous silica compound. Each of the contacting steps (h) and (p) may comprise the step of applying an external force to pass the solutions through the porous silica compound. The external force may be applied with a pump and the pump may be a suction pump. Steps (e), (h), (m) and (p) may be performed without using a centrifuge.

The method may further comprise the step of contacting the collected unbound protein with a biodetector. The method may further comprise the step of contacting the collected unbound nucleic acid with a biodetector. The steps (a)-(q) may be automated.

In another aspect, the invention provides a method for purifying proteins from a biological sample comprising the steps of: (a) providing a biological sample; (b) providing a chaotropic agent: (c) contacting the biological sample and the chaotropic agent; (d) providing a protein binding solution comprising a precipitating agent; (e) mixing a product of step (c) with the protein binding solution; (f) providing a porous silica compound configured to reversibly bind a protein; (g) contacting a product of step (e) with the porous silica compound; (h) providing a protein elution solution; (i) contacting the protein elution solution with the porous silica compound after step (g) to cause a majority of the protein bound to the porous silica compound to unbind; and (j) collecting the unbound protein.

The biological material may comprise cells or virus. The product of step (c) may comprise a waste solution from a chaotropic salt nucleic acid extraction procedure. The product of step (c) may comprise the biological sample suspended in a chaotropic solution. The chaotropic agent may be selected from a group consisting of urea, guanidine salts, and lithium perchlorate. The precipitating agent may comprise an alcohol. The alcohol may be selected from a group consisting of isopropanol, ethanol and methanol. The precipitating agent may comprise trichloroacetic acid or acetone. The protein binding solution may comprise a precipitating catalyst. The precipitating catalyst may comprise glycogen. The protein binding solution may comprise a detergent. The detergent may also act as a precipitating catalyst. The detergent may be selected from a group consisting of sodium dodecyl sulfate, polyoxyethylene sorbitan monooleate, and polyethylene glycol p-(1,1,3,3-tetramethylbutyl)-phenyl ether. The protein elution solution may comprise water and a salt. The protein elution solution may comprise a detergent, and the detergent may be a chemical selected from a group consisting of sodium dodecyl sulfate, polyoxyethylene sorbitan monooleate, and polyethylene glycol p-(1,1,3,3-tetramethylbutyl)-phenyl ether.

The method may further comprise the step of incubating a product of step (e) for a period of time. The period of time may be less than about 60 minutes. The period of time may be less than about five minutes. The method may further comprise the step of contacting a wash solution with the porous silica compound after step (g) and before step (i), and contacting the wash solution with the porous silica compound may be performed directly after step (g). The method may further comprise the step of drying the porous silica compound after the step of contacting the porous silica compound with the washing solution.

The porous silica compound may be in a form selected from the group consisting of a silica syringe filter, a silica matrix, a silica frit, a silica particulate column, and a silicate pipette tip. The porous silica compound may be borosilicate. The porous silica compound may comprise a paramagnetic material.

The contacting steps (i) or (g) may comprise the step of applying an external force to pass the product through the porous silica compound. This force may be applied with a pump, and the pump may be a suction pump. Steps (g), (i), and (j) may be performed without using a centrifuge. The method may further comprise the step of separating a fluid product of step (g) from the porous silica compound. The method may further comprise the step of contacting the collected unbound protein with a biodetector. The steps (a)-(i) may be automated.

In another aspect, the invention provides a kit for isolating nucleic acids and proteins from a single biological sample, the kit comprising: a nucleic acid binding solution, a protein binding solution, and a porous silica compound configured to reversibly bind a nucleic acid and a protein. The nucleic acid binding solution may comprise a chaotropic agent. The chaotropic agent may be selected from the group consisting of urea, guanidine salts, and lithium perchlorate. The nucleic acid binding solution may comprise a detergent, and the detergent may be selected from the group consisting of sodium dodecyl sulfate, polyoxyethylene sorbitan monooleate, and polyethylene glycol p-(1,1,3,3-tetramethylbutyl)-phenyl ether. The protein binding solution may comprise a precipitating agent. The precipitating agent may comprise an alcohol, and the alcohol may be selected from the group consisting of isopropanol, ethanol and methanol. The precipitating agent may comprise trichloroacetic acid or acetone. The protein binding solution may comprise a precipitating catalyst. The precipitating catalyst may comprise glycogen. The protein binding solution may comprise a detergent, and the detergent may be selected from the group consisting of sodium dodecyl sulfate, polyoxyethylene sorbitan monooleate, and polyethylene glycol p-(1,1,3,3-tetramethylbutyl)-phenyl ether.

The kit may further comprise a nucleic acid elution solution. The nucleic acid elution solution may comprise water and a salt. The kit may further comprise a protein elution solution. The protein elution solution may comprise water and a salt.

The porous silica compound may be in a form selected from the group consisting of a silica syringe filter, a silica matrix, a silica frit, a silica particulate column, and a silicate pipette tip. The porous silica compound may be borosilicate. The kit may not comprise a centrifuge.

BRIEF DESCRIPTION THE DRAWINGS

FIG. 2 is a gel analysis of a first example protein isolation.

FIG. 5 is a gel analysis of a third example protein isolation.

DETAILED DESCRIPTION

Figure 1:
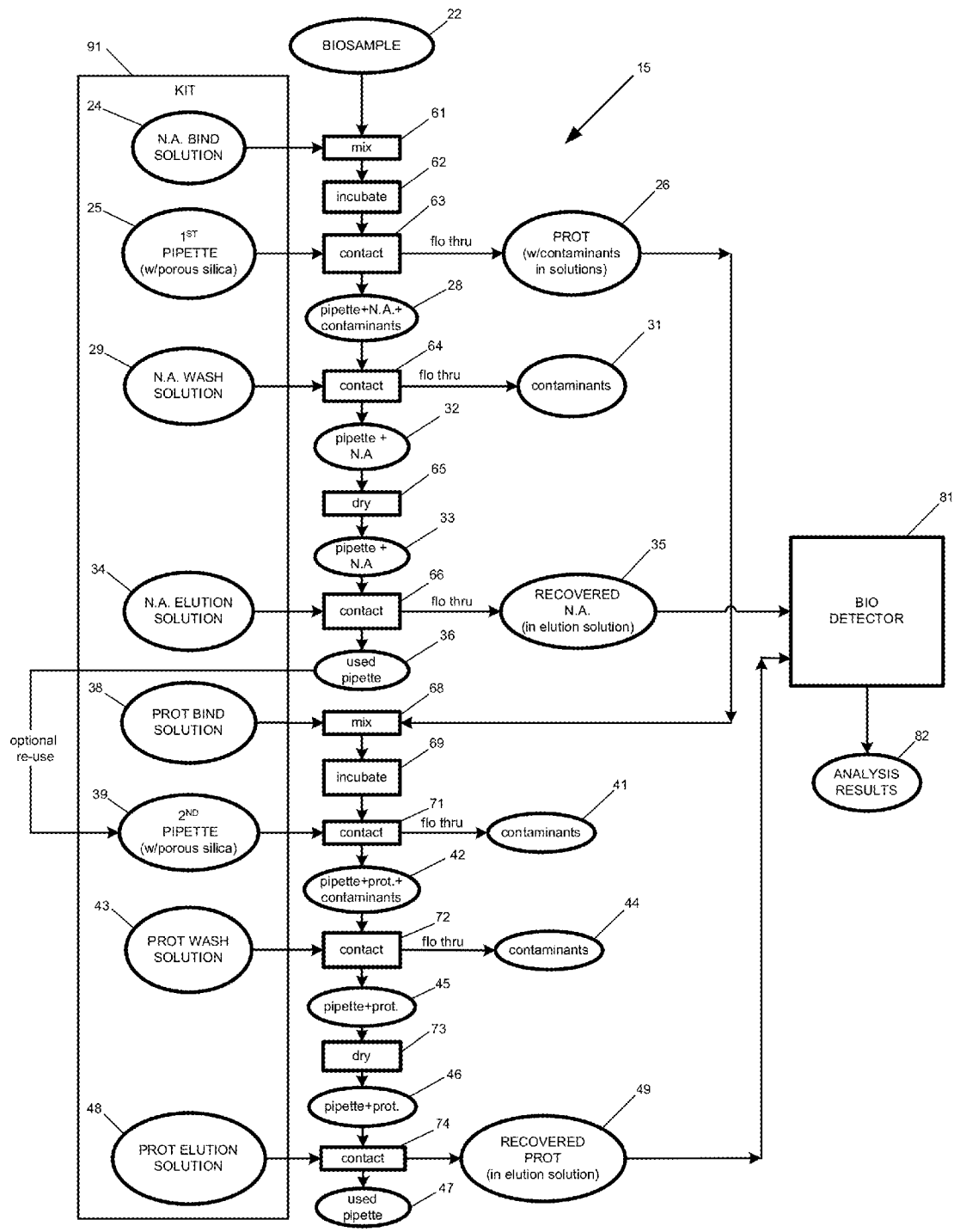
FIG. 1 is a schematic overview of an embodiment of the improved method.

At the outset, it should be clearly understood that like reference numerals are intended to identify the same structural elements, portions or surfaces consistently throughout the several drawing figures, as such elements, portions or surfaces may be further described or explained by the entire written specification, of which this detailed description is an integral part. Unless otherwise indicated, the drawings are intended to be read (e.g., cross-hatching, arrangement of parts, proportion, degree, etc.) together with the specification, and are to be considered a portion of the entire written description of this invention. As used in the following description, the terms "horizontal", "vertical", "left", "right", "up" and "down", as well as adjectival and adverbial derivatives thereof (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or axis of rotation, as appropriate.

Referring now to the drawings and, more particularly, to FIG. 1 thereof, this invention provides a method of isolating nucleic acids and protein from a biological sample, an embodiment of which is indicated at 15. In this embodiment, the process generally operates by selectively changing the relative affinity to silica of the nucleic acids and proteins in a solution.

As shown in FIG. 1, biological sample 22 is provided. Biological sample 22 should contain at least one protein or at least one nucleic acid, and it may be in the form of cells or viruses.

Nucleic acid binding solution 24 is then provided. The nucleic acid binding solution should effectively increase the affinity of nucleic acid to silica and/or decrease the solubility of the nucleic acid. Nucleic acid binding solution 24 also contains a chaotropic agent. In this embodiment, the chaotropic agent is guanidine thiocyanate at a concentration of 6 M. Alternatively, chaotropic agents such as urea or lithium perchlorate may be used. The chaotopic agent should disrupt the structure of molecules in the biological sample by interrupting hydrogen bonding, Van der Waals interactions, and hydrophobic effects. The nucleic acid binding solution may include a chaotropic agent combined with other compositions. For example, nucleic acid binding solution 24 may include a lysate to lyse cell membranes in biological sample 22.

Biological sample 22 is then mixed 61 with nucleic acid binding solution 24. The mixture is optionally incubated 62 for a period of time. The mixture of biological sample 22 with nucleic acid binding solution 24 is then contacted with porous silica compound 25. Porous silica compound 25 should be configured to reversibly bind a nucleic acid. In the preferred embodiment, pipette tips with a silica frit embedded within them are used as the silica compound. However, other silica compounds may be used, including a silica syringe filter, a silica matrix, a silica frit, or a silica particulate column. Also, the porous silica compound used may be made up of a paramagnetic material to aid in the step of separating the silica compound from the solutions they are contacted with.

The mixture is contacted 63 with silicate pipette 25 by sucking and pumping the fluid through the pipette tip with an automatic pipettor. This passing of the solution through the silica frit of the pipette is preferably repeated multiple times. The pipettor acts as both a pump and a suction device, and thereby allows any nucleic acids within the mixture to come into contact with the silica frit within the pipette tip. However, it is contemplated that other devices may be used to force the fluid through the silica compound. In this manner, the nucleic acids from biological sample 22 become bound to silicate pipette 25 as indicated at 28 and are thereby removed from and are no longer in solution. The proteins from the biological sample remain in the flow through solution 26 of the mixture. Flow through solution 26, hereafter referred to as nucleic acid binding flow through 26, is separated from the silicate pipette and used for protein extraction as described below.

Nucleic acid wash solution 29 is then contacted 64 with pipette tip 28 to remove any impurities which may be clinging to the silica or which are present in solution that remains bound to the silica frit by capillary action. In the preferred embodiment, a mixture of ethanol and acetone is used as the nucleic acid wash solution. The wash solution is passed through the silicate pipette tip several times using the automatic pipettor and is then discarded. After washing, silicate pipette 33 may be dried.

Next, nucleic acid elution solution 34 is contacted 66 with silicate pipette tip 33. In this embodiment, a mixture of water and salt is used as the nucleic acid elution solution. Nucleic acids have a higher affinity to the nucleic acid elution solution than to silica, causing the nucleic acids to unbind from the silica frit and enter the solution. Resulting solution 35 is then collected, thereby recovering nucleic acids isolated from original biological sample 22. The recovered nucleic acid may subsequently be used in biodetector 81. This nucleic acid isolation procedure has equivalent performance characteristics to the current nucleic acid isolation gold standard and the isolated nucleic acids are compatible with all tested downstream PCR-based detection platforms.

The proteins are extracted from nucleic acid binding flow through 26 collected earlier as follows. Nucleic acid binding flow through 26 is mixed 68 with protein binding solution 38. Protein binding solution 38 is a binding or precipitating agent that is adapted to assist in extracting protein from solution when it comes into contact with the porous silica. This mixture is then incubated 69 for less than 60 minutes. In certain applications, the incubation can be as short as five minutes or less without materially diminishing the efficacy of the process. While an incubation period of less than five minutes may be used, the effectiveness of protein binding solution 38 may decrease with shorter incubation periods. Example 5 below demonstrates that within 30 seconds of mixing with protein binding solution, the protein begins to precipitate in a form suitable for extraction. In this embodiment, protein binding solution 38 is isopropanol mixed with 2.5% sodium dodecyl sulfate and glycogen. Alternatively, other compounds may be used as the protein binding solution, such as isopropanol, ethanol, trichloroacetic acid, acetone or methanol. It is also often beneficial to have the protein binding solution include a precipitating catalyst. In this embodiment, glycogen acts as a precipitating catalyst in protein binding solution 38. The protein binding solution may also include a detergent. Examples of detergents which may be used include sodium dodecyl sulfate, polyoxyethylene sorbitan monooleate, and polyethylene glycol p-(1,1,3,3-tetramethylbutyl)-phenyl ether.

After incubation 69, the mixture is then contacted 71 with protein binding silica compound 39, which should be configured to reversibly bind a protein. In this embodiment, a new silicate pipette tip is used as the protein binding silica compound. However, other silica compounds may be employed, including a silica syringe filter, a silica matrix, a silica frit, a silica particulate column or borosilicate. Alternatively, rather than providing a new silica compound for the protein binding silica compound, used silica compound 36 from the previous nucleic acid extraction may be used as the protein binding silica compound.

As described above, a pipettor is used to pass the mixture through 71 the silica frit of silicate pipette 39 multiple times such that the proteins in the solution bind to the silica frit as indicated at 42. Flow through 41 is discarded. Protein wash solution 43 is then passed through 72 silicate pipette tip 42 to remove any impurities which may be clinging to the silica or which are present in any solution remaining bound to the silica frit due to capillary action. In this embodiment, isopropanol is used as protein wash solution 43. Again, wash solution 43 is passed through silicate pipette tip 42 several more times using the automatic pipettor, and is then discarded. After washing, the silicate pipette tip 45 may be dried 73.

Proteins are removed from dried silicate pipette tip 46 using protein elution solution 48, to which the proteins have a higher affinity than silica. In this embodiment, protein elution solution 48 is a mixture of water and salt. A detergent may also be added to the protein elution solution, such as sodium dodecyl sulfate, polyoxyethylene sorbitan monooleate, and polyethylene glycol p-(1,1,3,3-tetramethylbutyl)-phenyl ether. Protein elution solution 48 is passed through 74 silicate pipette tip 46 several times with the pipettor, causing the proteins to unbind from the silica frit and enter the solution. Resulting solution 49 is then collected, thereby recovering the proteins isolated from the rest of the original biological sample. As shown in Example 1 below, the process unexpectedly results in the extraction of a majority of the protein in the original sample and on average results in extraction of greater than 70% of the protein. Recovered protein 49 may be subsequently used in biodetector 81.

The described method resulted in a number of unexpected results. First, the process isolates both nucleic acids and protein from a sample without splitting the sample and without extraneous laboratory equipment. The process is a rapid one, allowing for isolation in less than 30 minutes. The process can be conducted in an in-line format, first isolating nucleic acids from the sample immediately followed by protein isolation, with nucleic acid clean-up and recovery occurring concurrent with protein isolation. The process is capable of isolating the majority of protein in a sample, with an average of 73%, and the recovered protein is immunoreactive. Thus, the process provides a means to rapidly isolate the two most prominent macromolecular classes of biological agent identifiers for use with the majority of downstream analyzers, thereby providing the user increased confidence in test results. The process may be electronically automated to improve speed, quality, and efficiency. Finally, the process extracts nucleic acids and protein from the same biological sample in high yield, without the use of dangerous reagents, and without the use of sophisticated laboratory equipment such as a centrifuge.

The invention also provides a kit, the preferred embodiment which is show in FIG. 1 at 91. The kit may be used to quickly isolate nucleic acids and/or protein from a biological sample without the need for a centrifuge or other expensive laboratory equipment. In the preferred embodiment, the kit generally comprises a nucleic acid binding solution, a protein binding solution, and a porous silica compound configured to reversibly bind a nucleic acid and/or a protein. The nucleic acid binding solution may be made up of a chaotropic agent only, or a chaotropic agent mixed with other elements. In this embodiment, the chaotropic agent is selected from the group consisting of urea, guanidine salts and lithium perchlorate, and includes a detergent, such as sodium dodecyl sulfate, polyoxyethylene sorbitan monooleate, and polyethylene glycol p-(1,1,3,3-tetramethylbutyl)-phenyl ether. In this embodiment, the protein binding solution includes a precipitating agent, and the precipitating agent is an alcohol such as isopropanol, ethanol or methanol. Alternatively, the precipitating agent may be trichloroacetic acid or acetone. The protein binding solution may also include a precipitating catalyst and a detergent. In this embodiment, the precipitating catalyst is glycogen.

The kit may also include a nucleic acid elution solution and a protein elution solution, such as water and a salt. The porous silica compound may be in a silica syringe filter, a silica matrix, a silica frit, a silica particulate column, a silicate pipette tip or borosilicate. The kit does not need to include a centrifuge.

Example 1

Separation of Total Protein and Subsequent Assay for Determining Percent Recovery The protein bovine serum albumin (BSA) was separated from the waste solution of a chaotropic salt nucleic acid extraction procedure. The concentration of BSA recovered in each elution fraction was then determined by Bradford Protein Assay. In this example, purified BSA protein was used as the starting biological sample.

Five hundred microliters of 1 mg/mL of BSA was mixed with 500 µL of 6 M guanidine thiocyanate. This solution was left to incubate for 10 minutes at room temperature. The incubated solution was then passed up and down through a TruTip™ silicate pipette tip (a 2 mL pipette tip with a silica-based frit embedded in it) available from Akonni Biosystems of Frederick, Md., five times using a Rainin EDP3 automatic pipettor set for a volume of 2 mL. This step acted as a mock nucleic acid isolation step. Any nucleic acids that were in solution would have bound to the silicate pipette tip, leaving behind the nucleic acid waste solution and proteins from the biological sample still suspended in the nucleic acid waste solution. A protein binding solution was prepared, comprising the mixture of isopropanol, 2.5% SDS, and 20 µg of the precipitating agent glycogen. 100 µL of the nucleic acid waste solution was added to 900 µL of the protein binding solution. This mixture was mixed by inversion until all of the SDS crystals were dissolved. The mixture was left to incubate for 15 minutes at room temperature. The entire 1 mL incubated sample was then passed up and down through a second silicate pipette tip five times. This allowed the protein in solution to bind to the silica frit of the second pipette tip. The bound protein was washed by passing 1 mL of isopropanol up and down the silicate pipette tip three times. The bound protein was dried to remove excess isopropanol simply by activating the automatic pipettor with the tip exposed to air and passing air over the frit. The bound protein was eluted from the silicate pipette using an elution buffer (phosphate buffered saline+ 0.1% SDS). The initial elution step was performed as follows; 150 µL of elution buffer was passed up and down through the silicate pipette three times. Approximately 100 µL of liquid was recovered following the final pass-through. The collected solution was labeled "elutions 1-3". Another 150 µL of elution buffer was passed once up and once down through the tip. The collected solution was labeled "elution 4". Again, another 150 µL of elution buffer was passed once up and once down through the tip and the collected solution labeled as "elution 5". The protein content of each elution was next measured by the conventional Bradford Protein Assay as described in Bradford, MM., Anal. Biochem. 72, 248 (1976). The entire process was repeated three times. The resulting data is summarized in Table 1. As indicated in Table 1, the process recovered greater than 50% of the protein and on average greater than about 70% of the protein in the original biological sample.

TABLE 1

Percent of Protein Recovery

| SAMPLE LABEL | PROTEIN [ ] (µg/mL) | % RECOVERED | TOTAL CUMULATIVE % RECOVERED |
|---|---|---|---|
| Elution 1-3 | 196.1 | 58.90% | 58.90% |
| Elution 4 | * | * | 58.90% |
| Elution 5 | * | * | 58.90% |
| Elution 1-3 | 229 | 68.80% | 68.80% |
| Elution 4 | 51.7 | 15.50% | 84.30% |
| Elution 5 | 35 | 10.50% | 94.80% |
| Elution 1-3 | 188 | 56.50% | 56.50% |
| Elution 4 | * | * | 56.50% |
| Elution 5 | 35 | 10.55% | 67.00% |

AVERAGE RECOVERY

| | |
|---|---|
| Average % Recovery of Elution 1-3 | 61.4% |
| Average % Recovery of Elution 4 | 5.17% |
| Average % Recovery of Elution 5 | 7.00% |
| Average Total % Recovery | 73.6% |

* indicates protein was undetected

Example 2

Isolation of the Sup35NM Yeast Prion Protein from the Waste Solution of a Nucleic Acid Extraction The method was shown to properly isolate the protein Sup35NM yeast prion from the waste solution of a nucleic acid extraction procedure. In this example purified Sup35NM yeast prion protein was used as the starting biological sample.

Purified Sup35NM was suspended at a concentration of approximately 150 µg/mL in 8 M urea. Twenty microliters of this solution was added to 180 µL of phosphate buffered saline (PBS). Two hundred microliters of the chaotropic agent guanidine thiocyanate, at 6 M, was added to the diluted Sup35NM sample and incubated at room temperature for 10 minutes. TruTip™ silicate pipette tips from Akonni Biosystems of Frederick, Md., were used as the porous silica substance for nucleic acids to bind to. The incubated sample was passed through the pipette tip five times using a Rainin EDP 3 automatic pipettor set for a volume of 2 mL. This step effectively acted as a mock nucleic acid isolation step. The remaining solution effectively acts as the nucleic waste solution from a chaotropic salt nucleic acid extraction procedure.

A protein binding solution was prepared by mixing 900 µL of isopropanol, 2.5% SDS and 20 µg of glycogen as a precipitating catalyst. 100 µL of the nucleic acid waste solution was added to the 900 µL of the protein binding solution. The resulting combination was mixed by inversion until all of the SDS crystals were dissolved. The mixture was left to incubate for 15 minutes at room temperature. The entire 1 mL sample was passed through a new silicate pipette tip five times. The flow thru solution was labeled "FT". The protein bound to the pipette tip was washed by passing 1 mL of isopropanol through the pipette tip three times. The resulting wash solution that passed through the pipette tip was labeled "wash". The captured protein was dried to remove excess isopropanol by passing air through the silicate pipette tip simply by activating the automatic pipettor with the tip exposed to air. The captured protein was eluted from the pipette tip using the protein elution solution (PBS+0.1% SDS). The initial elution step was performed as follows; 150 µL of elution buffer was passed up and down through the silicate pipette tip three times using the automatic pipettor. Approximately 100 µL of liquid was recovered following the final pass-through. This collected solution was labeled "elution 1". Another 150 µL of elution buffer was passed once up and once down with the automatic pipettor through the tip. This collected solution was labeled "elution 2". This concluded the protein isolation phase for the first sample.

The entire isolation process was repeated a second time with another Sup35NM yeast prion protein sample. However, the incubation time after addition to the isopropanol solution was increased to 30 minutes. Upon completion of the second isolation process, a second set of solutions labeled "wash", "FT", "elution 1", and "elution 2".

The two sets of solutions labeled "elution 1", "elution 2", "wash", and "FT" were then each tested for the presence of immunoreactive protein by conventional Western Blot. Fifty microliters of each solution was added to its own vial containing 50 µL of 2× SDS sample loading dye and heated to 95° C. for 10 minutes. Twenty microliters of each resulting sample was loaded into individual wells of two identical 10% SDS polyacrylamide gels. The samples were separated by application of a constant current of 40 mAmps for approximately 1.5 hours. One gel was stained with Coomassie stain. The second gel was used for the Western Blot. The gel was washed twice in distilled deionized water (ddH2O) followed by equilibration in Western transfer buffer. The gel was sandwiched with a PVDF membrane. Protein transfer to the PVDF membrane was performed using 12 volts for one hour. The membrane was washed once with ddH2O followed by three, five minute washes with PBST (PBS+tween). The membrane was blocked overnight at 4° C. in PBST+3% powdered milk. In the morning, the membrane was probed with 50 mL of a 1:10,000 of the rabbit anti-Sup35NM primary antibody diluted in PBST+2% powdered milk for 1.5 hours. The membrane was then washed three times with PBST to remove unbound primary antibody. Goat anti-rabbit secondary antibody conjugated to horseradish peroxidase (HRP) was used to identify the primary antibody. The membrane was incubated with the secondary antibody for one hour. This was followed by three washes with PBST. Standard HRP developer was then added and incubated for 30 minutes. The Western Blot was visualized using an Alpha Innotech FluorChem 9900. The resulting data are shown in FIG. 2. It can be readily seen that the protein from the original biological sample is present in the separated "elution 1". Further, the flow through (FT) and wash solutions did not contain a significant level of protein.

Example 3

Identification of Sup35NM from an Isolated Mixture of Protein

In this example, a mixture of the proteins Sup35NM and BSA were isolated. Western Blot was then performed to verify that the isolated proteins contain Sup35NM. Unless specifically mentioned otherwise, the materials and methods followed in this example were the same as the standard materials and methods.

Twenty five milliliters of Sup35NM (~150 µg/mL) was added to 225 µL PBS. To this, 250 µL of 1 mg/mL BSA was mixed, totaling 500 µL. The mixed protein sample was added to 500 µL of 6 M guanidine thiocyanate and incubated for 10 minutes. The sample was then passed through a silicate pipette (Akonni TruTip™) five times using a Rainin EDP 3 automatic pipettor set for a volume of 2 mL. This step effectively acted as a mock nucleic acid isolation step. The remaining solution effectively acted as the nucleic acid waste solution from a chaotropic salt nucleic acid extraction procedure.

A protein binding solution was prepared by mixing 900 µL of isopropanol, 2.5% SDS and 20 µg of glycogen as a precipitating catalyst. Two hundred microliters of the nucleic acid waste solution was removed and added to 900 µL of isopropanol, 2.5% SDS and 20 µg of glycogen. The sample was mixed by inversion until all of the SDS crystals were in solution. The sample was left to incubate for 15 minutes at room temperature. The entire 1 mL sample was passed through the silicate pipette tip five times. The flow through solution was labeled "FT". The protein bound to the pipette tip was washed by passing 1 mL of isopropanol through the pipette tip three times. The wash solution that passed through the pipette tip was labeled "wash". The captured protein was dried to remove excess isopropanol by passing air through the silicate pipette tip simply by activating the automatic pipettor with the tip exposed to air. The captured protein was eluted from the silicate pipette using an elution buffer (phosphate buffered saline+0.1% SDS). The initial elution step was performed as follows. One hundred fifty microliters of elution buffer was passed up and down through the silica pipette three times. Approximately 100 µl of liquid was recovered following the final pass-through. The collected solution was labeled "elution 1". Another 150 µl of elution buffer was passed, once, through the tip. The collected solution was labeled "elution 2".

Figure 3:
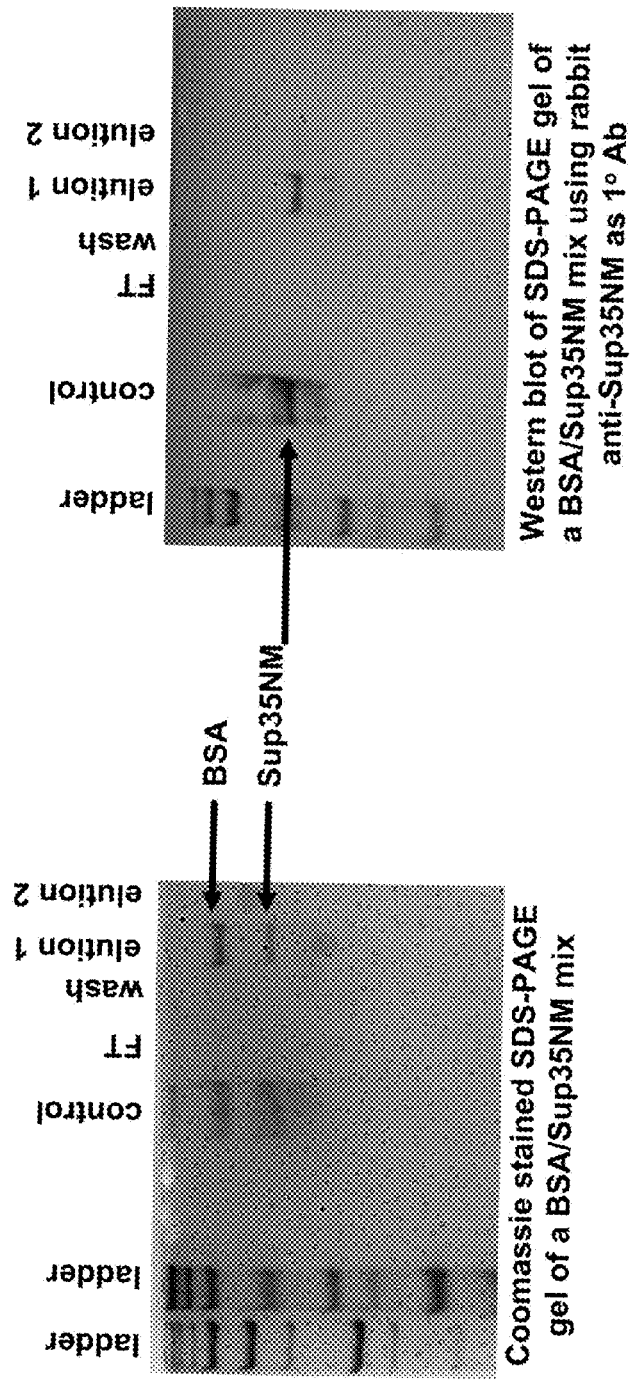
FIG. 3 is a gel analysis of a second example protein isolation.
Figure 4:
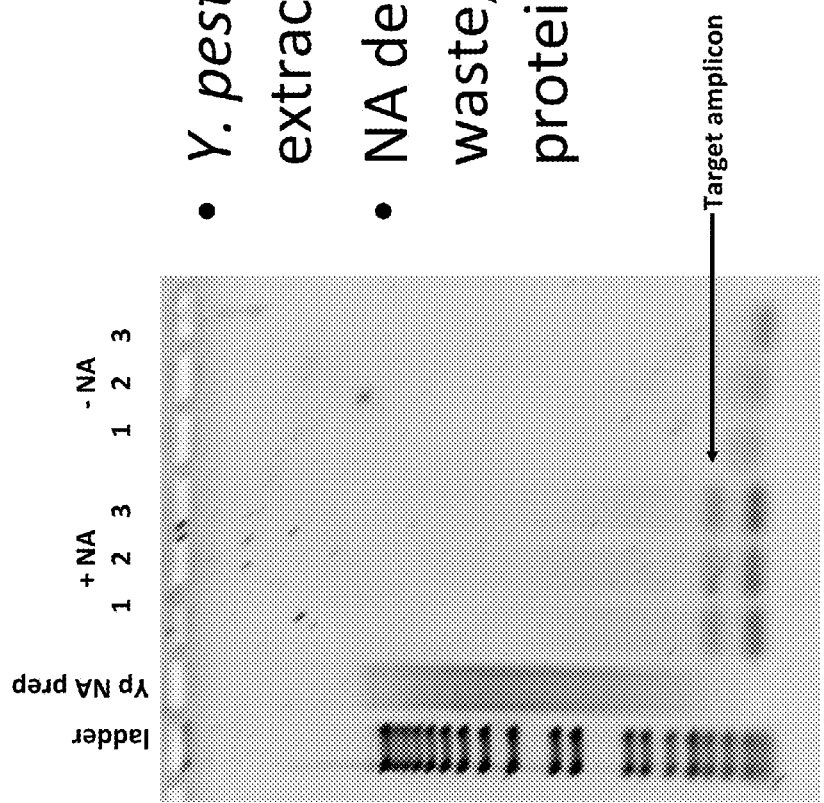
FIG. 4 is a gel analysis of a first example nucleic acid isolation.

The elutions labeled "elution 1", "elution 2", "wash", and "FT" were then tested for the presence of immunoreactive Sup35NM protein by Western Blot. Fifty microliters of each solution was added to its own vial containing 50 µL of 2× SDS sample loading dye and heated to 95° C. for 10 minutes. Twenty microliters of the resulting samples were loaded into individual wells of two identical 8% SDS polyacrylamide gels. The samples were separated by application of a constant current of 80 mAmps for 15 minutes followed by 40 mAmps for approximately one hour. One gel was stained with Coomassie stain. The second gel was used for the Western Blot. The gel was washed twice in distilled deionized water (ddH2O) followed by equilibration in Western transfer buffer. The gel was sandwiched with a PVDF membrane. Protein transfer to the PVDF membrane was performed using 12 volts for one hour. The membrane was washed once with ddH2O followed by three, five minute washes with PBST (PBS+tween). The membrane was blocked overnight at 4° C. in PBST+3% powdered milk. In the morning, the membrane was probed with 50 mL of a 1:10,000 of the rabbit anti-Sup35NM primary antibody diluted in PBST+2% powdered milk for 1.5 hours. The membrane was then washed three times with PBST to remove unbound primary antibody. Goat anti-rabbit secondary antibody conjugated to horseradish peroxidase (HRP) was used to identify the primary antibody. The membrane was incubated with the secondary antibody for one hour. This was followed by three washes with PBST. Standard HRP developer was then added and incubated for 30 minutes. The Western Blot was visualized using an Alpha Innotech FluorChem 9900. The resulting data is shown in FIG. 3. It can be readily seen that the Sup35NM protein from the original biological sample is present in the separated "elution 1". Further, the flow thru (FT) and wash solutions did not contain a significant level of Sup35NM protein.

Example 4

Nucleic Acid and Protein Recovery and Specific Antigen Identification from Cell Sample of *Yersinia pestis*

Immunoreactive protein from *Y. pestis* was identified from a protein isolation extraction of whole cells. One milliliter of *Y. pestis* was grown statically at 37° C. for four days. Cells were harvested by centrifugation for five minutes at 14,000 rpm. The cell titer was $1.51\times10^{10}$ cfu/mL. The cells were resuspended in 600 μL of PBS. Five hundred microliters of this solution was added to 500 μL of 6 M guanidine thiocyanate and mixed. The mixture was then incubated for 10 minutes at room temperature. The mixture was then passed up and down through a silicate pipette tip (Akonni TruTip™) five times to cause the *Y. pestis* nucleic acids to bind to the silicate pipette tip. The flow through was collected.

Approximately 1 mL of wash buffer (Akonni Biosystems "Wash Buffer" product #300-10004) was then passed up and down through the silicate pipette tip five times. The flow through was discarded. Two milliliters of air was then passed in and out through the pipette tip five times using a pipettor to dry the silica frit. The nucleic acids then bound to the silica frit were recovered by passing a nucleic acid elution solution (Akonni Biosystems "Elution Buffer" product #300-10005) five times up and down through the silicate pipette. The isolated nucleic acids were amenable to PCR amplification as seen in FIG. 4.

The flow through from the nucleic acid isolation was then processed to isolate total protein content according to the following steps. One hundred microliters of the flow through was added to 900 μL of isopropanol, 2.5% SDS, and 20 μg of glycogen. The sample was mixed by inversion until all of the SDS crystals were in solution. The sample was left to incubate for 15 minutes at room temperature. The entire 1 mL sample was the passed through a new silicate pipette five times. The flow through was collected and labeled "flow thru". The captured protein was washed by passing 1 mL of isopropanol through the silicate pipette tip three times. The fluid product was collected and labeled "wash". The captured protein was dried to remove excess isopropanol by passing air through the silicate pipette tip using an automatic pipettor. The captured protein was eluted from the silicate pipette using the elution buffer (phosphate buffered saline+0.1% SDS). The initial elution step was performed as follows; 150 μl of elution buffer was passed up and down through the silica-based frit three times. Approximately 100 μl of liquid was recovered following the final pass-through. The collected solution was labeled "elution 1". Another 150 μl of elution buffer was passed, once, through the tip. The collected solution was labeled "elution 2". Again, 150 μl of elution buffer was passed, once, through the tip. The collected solution was labeled as "elution 3".

The elutions were then tested for the presence of immunoreactive *Y. pestis* protein by Western Blot. Fifty microliters of elutions 1 and 2 were added to 50 μl of 2× SDS sample loading dye and heated to 95° C. for 10 minutes. The wash and flow thru from the test was treated as per the elutions. Twenty microliters of the resulting samples were loaded into individual wells of two identical 10% SDS poly-acrylamide gels. The samples were separated by application of a constant current 40 mAmps for approximately two hours. One gel was stained with Coomassie stain. The second gel was used for the Western Blot. The gel was washed twice in distilled deionized water (ddH2O) followed by equilibration in Western transfer buffer. The gel was sandwiched with a PVDF membrane. Protein transfer to the PVDF membrane was performed using 12 volts for one hour. The membrane was washed once with ddH2O followed by three, five minute washes with PBST (PBS+tween). The membrane was blocked overnight at 4° C. in PBST+3% powdered milk. In the morning, the membrane was probed with 50 mL of a 1:10,000 of the rabbit anti-*Y. pestis* (R-PESTIS from Department of Defense Critical Reagents Program (CRP)) primary antibody diluted in PBST+2% powdered milk for 1.5 hours. The membrane was washed three times with PBST to remove unbound primary antibody. Goat anti-rabbit secondary antibody conjugated to horseradish peroxidase (HRP) was used to identify the primary antibody. The membrane was incubated with the secondary antibody for one hour. This was followed by three washes with PBST. Standard HRP developer was then added and incubated for 30 minutes. The Western Blot was visualized using an Alpha Innotech FluorChem 9900. The resulting data is shown in FIG. 5.

Example 5

Isolation of Protein from a Silica-Based Syringe Filter

Unlike Examples 1-4, this example used a silica-based syringe filter, rather than a silicate pipette tip, and the entire 1 mL sample was mixed with isopropanol buffer, not the typical 100 µl as described in examples 1-4. The volumetric change, from 1 mL to 10 mL, required an alteration in the form of the protein capture matrix. In this case, a 25 mm syringe filter composed of borosilicate with a 2.7 µm pore size was utilized.

In this example, 500 µl of 1 mg/mL BSA was mixed with 500 µl of 6 M guanidine thiocyanate and incubated at room temperature for 10 minutes. This 1 mL sample was passed through a TruTip™ pipette tip five times to simulate nucleic acid isolation.

Figure 6:
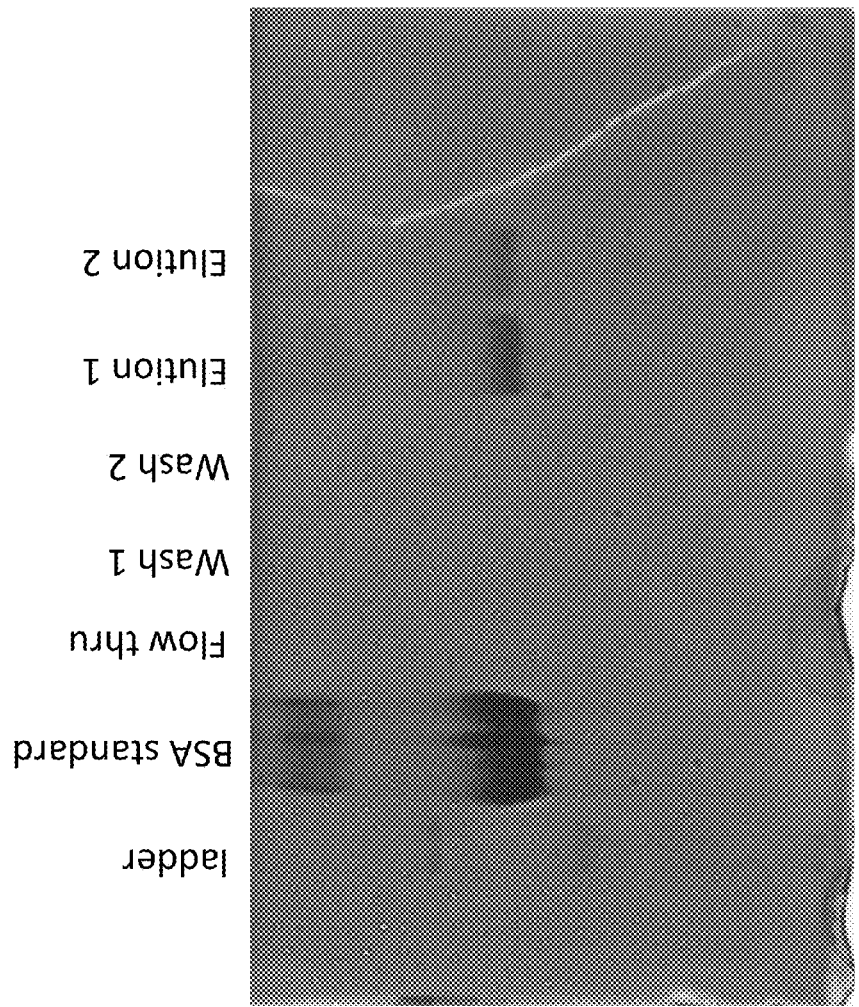
FIG. 6 is a gel analysis of a fourth example protein isolation.

The entire flow thru was then added to 9 mL of isopropanol, 1% SDS and 20 µg/mL glycogen and mixed by inversion until the SDS crystals were completely dissolved. The sample was incubated at room temperature for 10 minutes. Precipitate was visible within 30 seconds of incubation. The entire volume of liquid (10 mL) was loaded into a 10 cc syringe. The silica-based syringe filter was fastened to the syringe on the "top" position. A second 10 cc syringe was fastened to the opposite end of the syringe filter. The liquid was passed through the syringe filter, back and forth, five times. The final passage resulted in the entire volume residing in the syringe opposite to the one it started in. Both 10 cc syringes were removed and two fresh syringes fastened to the syringe filter with the one in the "top" position containing 10 mL of isopropanol. The isopropanol was passed back and forth five times ending in the opposite syringe that it started. This wash step was repeated one more time. To dry the filter, a fresh syringe was fastened to the "top" position and air was passed through the syringe filter approximately 20 times until it appeared dry by visual inspection. The captured protein was eluted from the syringe filter using the same elution buffer as examples 1-4. One milliliter of elution buffer was loaded into a 2 cc syringe and attached to the "top" position. An empty 2 cc syringe was attached to the other end and the elution buffer passed back and forth through the syringe filter five times. The final passage resulted in the elution buffer residing in the "bottom" syringe. This syringe was removed and the elution was injected into a microcentrifuge tube and labeled elution 1. The elution step was repeated one more time resulting in elution 2. The elutions, flow thru and washes were all tested for the presence of BSA by SDS poly-acrylamide gel electrophoresis. The gel was stained with coomassie stain and visualized using an Alpha Innotech, FluorChem 9900. The resulting data is shown in FIG. 6. The data shows that BSA is only present in the elutions.

The present invention contemplates that many changes and modifications may be made. Therefore, while the presently-preferred form of the method and kit have been shown and described, and several embodiments discussed, persons skilled in this art will readily appreciate that various additional changes and modifications may be made without departing from the spirit of the invention, as defined and differentiated by the claims.

What is claimed is:
1. A method for recovering nucleic acids and proteins from a biological sample comprising the steps of:
   (a) providing a biological sample;
   (b) providing a nucleic acid binding solution;
   (c) mixing said biological sample with said nucleic acid binding solution;
   (d) providing a first porous silica compound configured to reversibly bind a nucleic acid;
   (e) contacting a product of step (c) with said first porous silica compound;
   (f) separating a fluid product of step (e) from said first porous silica compound;
   (g) providing a nucleic acid elution solution;
   (h) contacting said nucleic acid elution solution with said first porous silica compound after step (f) to cause a majority of said nucleic acid bound to said porous silica compound to unbind;
   (i) collecting said unbound nucleic acid;
   (j) providing a protein binding solution;
   (k) mixing said fluid product of step (f) with said protein binding solution;
   (l) providing a protein binding porous silica compound configured to reversibly bind a protein;
   (m) contacting a product of step (k) with said protein binding porous silica compound;
   (n) separating a fluid product of step (m) from said protein binding porous silica compound;
   (o) providing a protein elution solution;
   (p) contacting said protein elution solution with said protein binding porous silica compound after step (m) to cause a majority of said protein bound to said protein binding porous silica compound to unbind; and
   (q) collecting said unbound protein.

2. The method of claim 1, wherein said nucleic acid binding solution comprises a chaotropic agent.

3. The method set forth in claim 1, wherein said nucleic acid binding solution comprises a lysate.

4. The method of claim 2, wherein said chaotropic agent is selected from a group consisting of urea, guanidine salts, and lithium perchlorate.

5. The method of claim 1, wherein said nucleic acid binding solution comprises a detergent.

6. The method of claim 1, wherein said first porous silica compound is in a form selected from a group consisting of a silica syringe filter, a silica matrix, a silica frit, a silica particulate column, and a silicate pipette tip.

7. The method of claim 1, wherein said nucleic acid elution solution comprises water and a salt.

8. The method of claim 1, wherein said protein binding solution is selected from a group consisting of isopropanol, ethanol, trichloroacetic acid, acetone, and methanol.

9. The method of claim 1, wherein said protein binding solution comprises a precipitating catalyst.

10. The method of claim 9, wherein said precipitating catalyst comprises glycogen.

11. The method of claim 1, wherein said protein elution solution comprises water and a salt.

12. The method of claim 1, and further comprising the step of incubating a product of step (k) for a period of time.

13. The method of claim 12, wherein said period of time is less than about 60 minutes.

14. The method of claim 13, wherein said period of time is less than about five minutes.

15. The method of claim 1, and further comprising the step of contacting a wash solution with said first porous silica compound after step (e) and before step (h).

16. The method of claim 15, wherein said wash solution comprises ethanol or acetone.

17. The method of claim 1, and further comprising the step of contacting a wash solution with said protein binding porous silica compound after step (m) and before step (p).

18. The method of claim 17, wherein said wash solution comprises isopropanol.

19. The method of claim 1, wherein said protein binding porous silica compound is in a form selected from a group consisting of a silica syringe filter, a silica matrix, a silica frit, a silica particulate column, and a silicate pipette tip.

20. The method of claim 1, wherein said protein binding porous silica compound is borosilicate.

21. The method set forth in claim 1, wherein said first porous silica compound and said protein binding porous silica compound are the same.

22. The method of claim 1, wherein each of said first porous silica compound and protein binding porous silica compound comprises a paramagnetic material.

23. The method of claim 1, wherein each of said contacting steps (e), (m), (h), and (p) comprise the step of applying an external force to pass said products through said porous silica compound.

24. The method of claim 23, wherein said force is applied with a pump.

25. The method set forth in claim 1, and not comprising the step of using a centrifuge in any of steps (e), (h), (m) and (p).

26. The method of claim 1, and further comprising the step of contacting said collected unbound protein with a biodetector.

27. The method of claim 1, and further comprising the step of contacting said collected unbound nucleic acid with a biodetector.

28. The method of claim 1, wherein said steps (a)-(q) are automated.

29. A method for purifying proteins concurrently or in-line with nucleic acid recovery from the same biological sample, the method comprising the steps of:
(a) providing a biological sample;
(b) providing a chaotropic agent:
(c) contacting said biological sample and said chaotropic agent;
(d) providing a protein binding solution comprising a precipitating agent;
(e) mixing a product of step (c) with said protein binding solution;
(f) providing a protein binding porous silica compound configured to reversibly bind a protein;
(g) contacting a product of step (e) with said protein binding porous silica compound;
(h) separating a fluid product of step (g) from said protein binding porous silica compound;
(i) providing a protein elution solution;
(j) contacting said protein elution solution with said protein binding porous silica compound after step (h) to cause a majority of said protein bound to said protein binding porous silica compound to unbind;
(k) collecting said unbound protein;
(l) providing a nucleic acid binding solution;
(m) mixing said fluid product of step (h) with said nucleic acid binding solution;
(n) providing a nucleic acid porous silica compound configured to reversibly bind a nucleic acid;
(o) contacting a product of step (m) with said nucleic acid porous silica compound;
(p) separating a fluid product of step (o) from said protein binding porous silica compound;
(q) providing a nucleic acid elution solution;
(r) contacting said nucleic acid elution solution with said nucleic acid porous silica compound after step (o) to cause a majority of said nucleic acid bound to said nucleic acid porous silica compound to unbind; and
(s) collecting said unbound nucleic acid.

30. The method of claim 1, wherein said chaotropic agent is selected from a group consisting of urea, guanidine salts, and lithium perchlorate.

31. The method of claim 1, wherein said precipitating agent comprises an alcohol.

32. The method of claim 31, wherein said alcohol is selected from a group consisting of isopropanol, ethanol and methanol.

33. The method of claim 1, wherein said precipitating agent comprises trichloroacetic acid or acetone.

34. The method of claim 1, wherein said protein binding solution comprises a precipitating catalyst.

35. The method of claim 34, wherein said precipitating catalyst comprises glycogen.

36. The method of claim 1, wherein said protein elution solution comprises water and a salt.

37. The method of claim 1, and further comprising the step of incubating a product of step (e) for a period of time.

38. The method of claim 37, wherein said period of time is less than about 60 minutes.

39. The method of claim 38, wherein said period of time is less than about five minutes.

40. The method of claim 1, and further comprising the step of contacting a wash solution with said porous silica compound after step (g) and before step (i).

41. The method of claim 1, wherein said porous silica compound is in a form selected from a group consisting of a silica syringe filter, a silica matrix, a silica frit, a silica particulate column, and a silicate pipette tip.

42. The method of claim 1, wherein said porous silica compound is borosilicate.

43. The method set forth in claim 1, wherein said porous silica compound comprises a paramagnetic material.

44. The method of claim 1, wherein said contacting steps (g) and (i) comprise the step of applying an external force to pass said product through said porous silica compound.

45. The method of claim 44, wherein said force is applied with a pump.

46. The method set forth in claim 1, and not comprising the step of using a centrifuge in any of steps (g), (i), or (j).

47. The method of claim 1, and further comprising the step of separating a fluid product of step (g) from said porous silica compound.

48. The method of claim 1, and further comprising the step of contacting said collected unbound protein with a biodetector.

49. The method of claim 1, wherein said steps (a)-(i) are automated.

* * * * *